(12) United States Patent  (10) Patent No.: US 6,950,839 B1
Green et al.  (45) Date of Patent: Sep. 27, 2005

(54) NATURE'S FRIEND

(76) Inventors: Alesandra Green, 942 Trimble Pl., Sagamore Hills, OH (US) 44067; Debbie D. Fleming-Mixon, 7215 Blackwell Dr., Oakwood Village, OH (US) 44146

( * ) Notice: Subject to any disclaimer, the term of this patent is extended or adjusted under 35 U.S.C. 154(b) by 610 days.

(21) Appl. No.: 09/948,694

(22) Filed: Sep. 10, 2001

Related U.S. Application Data

(60) Provisional application No. 60/260,652, filed on Jan. 11, 2001.

(51) Int. Cl.[7] .......................... G06F 15/00; A61B 17/42
(52) U.S. Cl. ...................... 708/200; 606/119
(58) Field of Search ............................... 708/100, 132, 708/142, 200; 368/28, 23; 600/551; 606/119

(56) References Cited

U.S. PATENT DOCUMENTS

| 4,367,527 A | * | 1/1983 | Desjacques | 708/132 |
| 5,058,085 A | * | 10/1991 | Lawler | 368/28 |
| 5,233,547 A | * | 8/1993 | Kapp et al. | 708/106 |
| 5,606,535 A | * | 2/1997 | Lynn | 368/223 |
| 5,777,905 A | * | 7/1998 | Dowdle et al. | 708/142 |
| 5,836,890 A | * | 11/1998 | Jackson | 600/551 |
| 6,600,696 B1 | * | 7/2003 | Lynn | 368/23 |

* cited by examiner

Primary Examiner—Todd Ingberg
Assistant Examiner—Chat C. Do
(74) Attorney, Agent, or Firm—Clarence L. Albritton

(57) ABSTRACT

An electronic device for recording a woman's menstrual cycle, recalling each recorded cycle and updating each cycle with respect to normal and abnormal menstrual flow; a frequency button is provided to record the average number of days between periods; a projection button is provided to project future period dates and is used in combination with an override button which recalls the number of days between periods and is usable to customize future period projection dates to an individual user's natural health response by setting and entering a new override value; an exam button is included to set and store breast and Papanicolaou, cervico-vaginal or PAP smear exam dates and a reminder message is displayed for five seconds when the device is turned on once the stored exam dates are within two months of termination.

17 Claims, 13 Drawing Sheets

NATURE'S FRIEND

Applicants claim the benefit of Provisional Application Ser. No. 60/260,652 filed on Jan. 11, 2001.

The present invention relates to a compact electronic device for keeping an accurate account of a woman's menstrual cycle with means for storing, recalling, updating, monitoring, projecting and customizing cycle and other health-related dates.

BACKGROUND OF THE INVENTION

Monitoring a menstrual cycle is of utmost importance to women for obvious reasons. Monitoring one's menstrual cycle is an alternative form of contraception. Due to the present rise in the cost of living, proliferation is not a viable option. An abnormal or heavy cycle is usually a sign of a health problem. Spotting, on the other hand, is normally seen as a sign of the beginning of a cycle, the end of a cycle, or the sign of a pregnancy, among other things.

In this respect, women, especially young girls, have a need for a simple device whereby they can recall their period dates, update their period flow rate and recall their period data in a flash. Moreover, a projected period date can be used as a guide as to when one needs to carry protective pad means in anticipation of a period to avoid a disappointing or an embarrassing outcome.

The patent to Lynn, U.S. Pat. No. 5,606,535 shows one of many ways to monitor a woman's menstrual cycle. The electronic device or chronometer has means for displaying menstrual, ovulation and menopausal cycles. This device differs from the present invention in one of many ways because it does not have means for updating a woman's abnormal flow rate cycle for later recall; this recall could be of utmost importance to a gynecologist in determining whether there is a minor gynecological problem or a major problem in the interior of the woman's body such as a uterine tumor. Moreover, the chronometer device does not display means for customizing the device to an individual's chronologically abnormal cycle projection. Additionally, there is no provision for recording PAP (named for Dr. Papanicolaou and herein shall mean cervicovaginal smear or PAP smear) and breast exam dates with automatic reminder message display, at start up, when the recorded dates are within sixty days of termination.

The patent to Dowdle, et al., U.S. Pat. No. 5,777,905 shows an electronic calculator structured to accept data relating to the last menstrual period, conception date, estimated date of confinement, reference date (defaulted to the date of entry) and estimated gestational development, noting particularly the emphasis placed on fetal development and birth. This invention is set such that the entrance into the calculator of any one or more variables of the five listed above, the calculator automatically calculates the remaining four or fewer variables, respectively.

The present invention does not employ the calculation of variables by the application of one or two other variables as described by Dowdles et. al. The present invention further differs in providing means for setting exam dates far in advance for pap PAP and breast with an included reminder message displayed when the device is activated within sixty days of the termination date; further, the present device includes key means for customization of projected menstrual dates according to an individual's health response. The present invention is customized with a recall key to recall menstrual periods stored in the system of the device; moreover, in the present invention, the recorded periods are recalled and augmented with a flow-rate pattern such as light, normal or heavy and stored for later recall with a more meaningful gynecological record for the evaluation of a woman's health.

The patent to Jackson, U.S. Pat. No. 5,836,890 shows a compact fertility predictor with stored instructional sequences with means to calculate chances of pregnancy. The patent to Thabet et al., U.S. Pat. No. 5,310,994 shows a fertility period calculator which operates with two rotatable disk.

While the present invention does not emphasize fertility calculation or prediction, certain stored information such as spottiong could be used in that sense. The present invention stores and recalls information that is considered to be more meaningful to a medical practitioner as a medical evaluation tool.

SUMMARY OF THE INVENTION

The present invention is a compact digital controller with real-time clock with battery back-up, non-volatile memory, computer interface, keypad interface, display driver and power supply therefore, two-line display and an especially designed key pad including: ten numeric keys and various function keys or buttons including a set-clock key, on/off and enter keys; a period recall key and three period update keys (light, normal and heavy); a frequency key, a projection and an override key; spotting, spotting recall, exam and clear keys or buttons.

It is an object of the present invention to provide women from approximately age thirteen through menopause, with a tool for keeping an accurate record of their monthly menstrual cycle in addition to other areas of health maintenance, such as, to record, recall and update each monthly period flow as to light, heavy or normal at the activation of specific keys provided on the key pad. A projection key or button is provided to display eleven additional period dates after the first date.

It is an object of the present invention to provide an override variable to customize future projections in response to variations in a woman's cycle without turning the device off and on again to initialize the system.

It is a further object of the present invention to provide a specific function key to record spotting dates and a spotting recall function key to scroll through recalls up to three hundred and sixty-five.

A further object is to provide an exam function key for storing or rewriting and recalling alternately PAP exam and breast exam dates; and, further providing a five-second reminder message display of each date at the initial activation of the device within sixty day of the termination of said exam dates.

It is yet a further object of the invention to provide a compact storable gynecological device provided with an operational electronic system that is simplistic in operation and structure, capable of downloading into the user's personal computer, with convenient display and operational button means specific to the needs of women from about thirteen or younger to menopause.

DETAILED DESCRIPTION OF THE INVENTION

The present invention "Nature's Friend" is a gynecological device having an electronic system designed to be user friendly for women, while not limited thereto, from approximately thirteen or younger to menopause, to monitor and spot gynecological problems from flow rate information recorded and stored for recall in the device. The present invention has the appearance of a hand-held calculator; however, it should be understood that the function of the present invention incorporates technology with the recording of a female user's menstrual cycle information augmented with specific flow rates which are considered vital to a medical practitioner for an on-the-spot or further test evaluation of the user's health problems. The present invention is better understood by reference to the various figures of the drawings.

Figure 1:
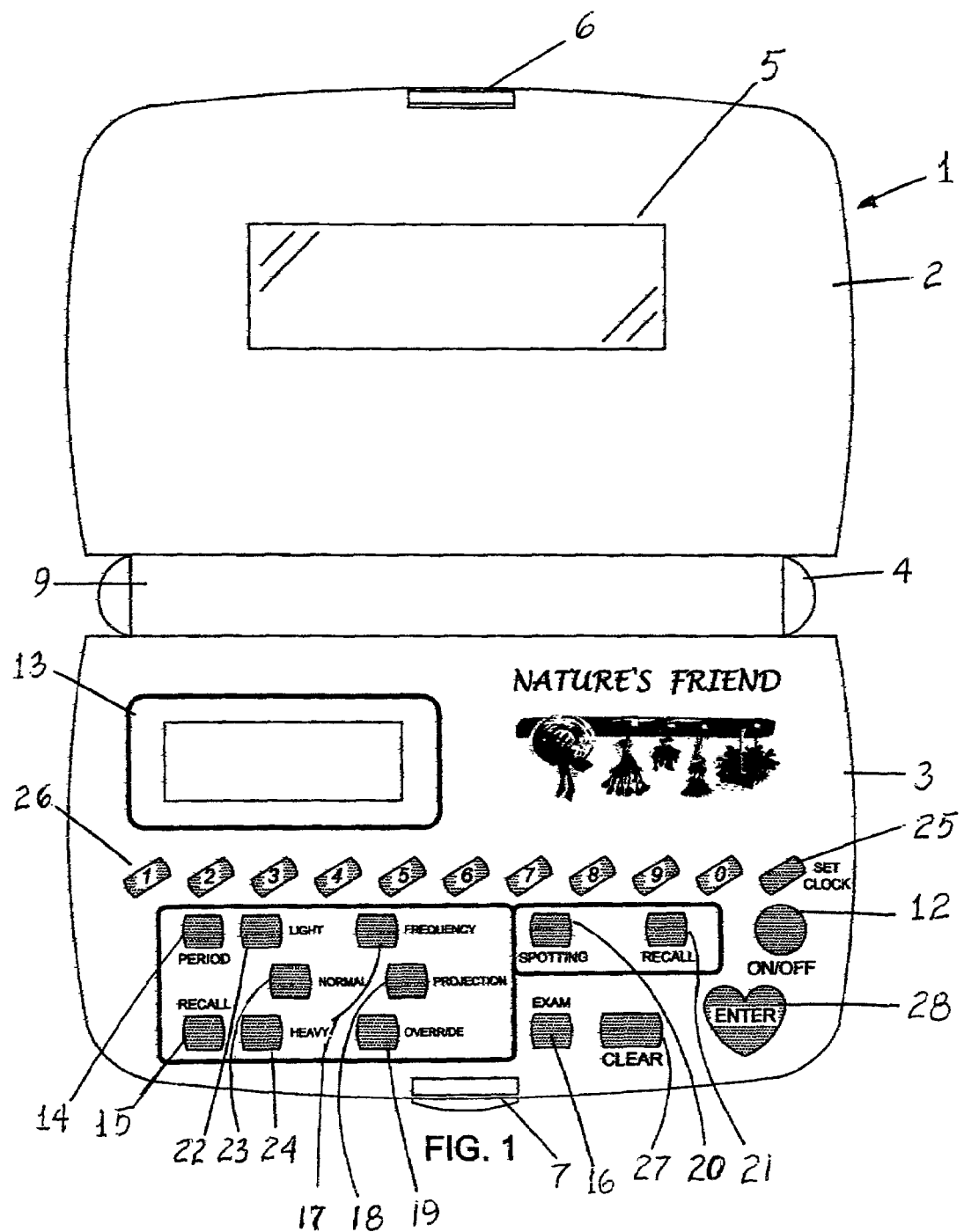
FIG. 1 is a top plan view of the present invention in an open position.

FIG. 1 shows a hand-held device 1 in an opened position comprising a housing consisting of upper and lower plastic closure members 2 and 3 cover and base), respectively, of any desired rigidity within the range of soft to hard and rigid connected by hinge member 4; each portion of said housing, lower and upper, has proximal and distal ends. The proximal ends are attached by said hinge means 4. Said hinge means is constructed and arranged to provide a housing for batteries to power the device. Upper housing portion, cover 2, is provided with a mirror 5 in an interior portion thereof. The distal end of upper housing portion 2 is provided with clip 6 for mechanical communication with locking means 7 arranged at the distal end of said lower housing portion, base 3.

Base 3 is provided with a two-line Liquid Crystal display (LCD) 13; moreover, function keys and Arabic, numeric keys 26 are also provided there below. Said LCD is initialized to display month day and year (mm/dd/yy) on a first line and time on a second, lower line. Numeric Keys 26 are used to enter all numerical information including dates of menstrual cycle in the mm/dd/yy mode. Clock set key 25 is used to set or adjust the date and time of real-time clock 32 with the numeric keys and the inputted information is entered by activating the enter key 28, when it is correct. Clear key 27 is used when numeric information is entered incorrectly.

When set clock key 25 is depressed once by a user, dispay 13 prompts the user, by flashing, to enter a date (mm/dd/yy) on the first line of the two-line display; when the button is depressed a seond time, the system prompts the user to enter time on the second line of the two-line display.

The device has a period key 14; this key is used, with numeric keys, to record the date of a woman's period each month. Period dates, up to 12, are stored in non-volatile memory 33 and can be recalled therefrom. Each period date is recalled by pressing recall key 15; once a period dated is recalled, the display is augmented, by selection, with the period flow rate for the date recalled. This is accomplished through the utilization of flow rate keys 22, 23 and 24.

Spotting is not a common gynecological problem with women. However, spotting button 20 is provided on the device to record spotting occurrences. Spotting dates up to 365 are stored in non-volatile memory 33 and can be recalled; moreover, recall button 21 is provided for spotting occurences so that a woman can use the device to check the frequency of said spotting occurences. Because each woman has a body that functions differently, a frequency button is provided to ascertain the number of days between a user's cycle information. Once several period dates have been entered into the system of the device, the activation of frequency button 17 yields two frequency types. When the frequency button is activated once, the device will exhibit on display screen 13 the number of days between the last two period recall dates entered into the system of the device; if button 17 is activated a second time, the system of the device will display on screen 13 the average number of days between all stored recall period dates entered into the system of the device. Since it is the desire of every woman to have a device that is both user friendly and user specific, device 1 is provided with an override function key 19 to make internal cycle calculations user specific. The activation of key 19 yields a default value of 28 days on LCD display screen 13.

To make the device user specific at this point, the user will select a new override number between fifteen and thirty-five (15 and 35) which is specific to her cycle; this new override number is ascertainable in reference to the frequency calculated from the total number of at least three recall period dates entered into the system of the device.

Examination key 16 is used to input a PAP exam date and a breast exam date; the exam dates are displayed alternately with subsequent key operations once these dates are entered; these values are initialized to a fixed pre-determined value each time power key 12 is pressed and the device is energized. The exam dates can be changed by the operation of exam key 16 and numeric keys 26 to enter a new date to be displayed; moreover, the system checks for exam dates. When exam dates are within sixty days of scheduled time date wise, the system is programmed to display a reminder message for each scheduled appointment for a period of five seconds and then the date and time from the real time clock is displayed.

A projection key is provided on the device to give a user the ability to determine future period dates from the user's specific period dates entered into the device.

Clear key 27 is used to cancel information set for entry into the system when there is an error in the information.

Enter key 28 allows the user to store information into the system.

Figure 2:
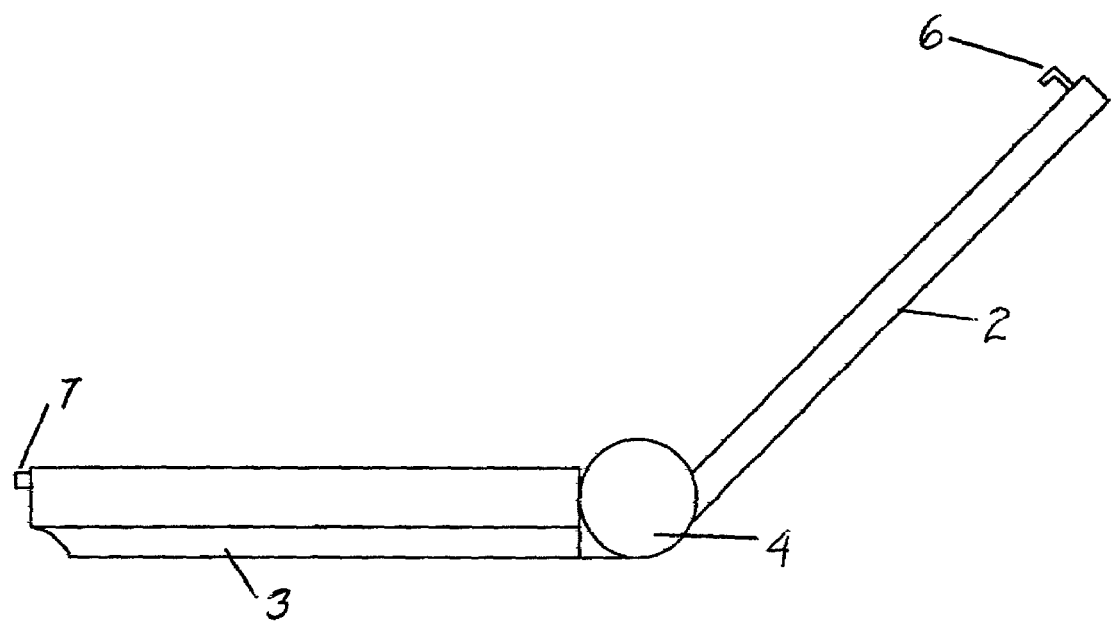
FIG. 2A is a side elevational view of the invention of FIG. 1
FIG. 2B is a side view of the present invention in a closed position.
FIG. 2C is a botton view of the invention of FIG. 2B.
Figure 2:
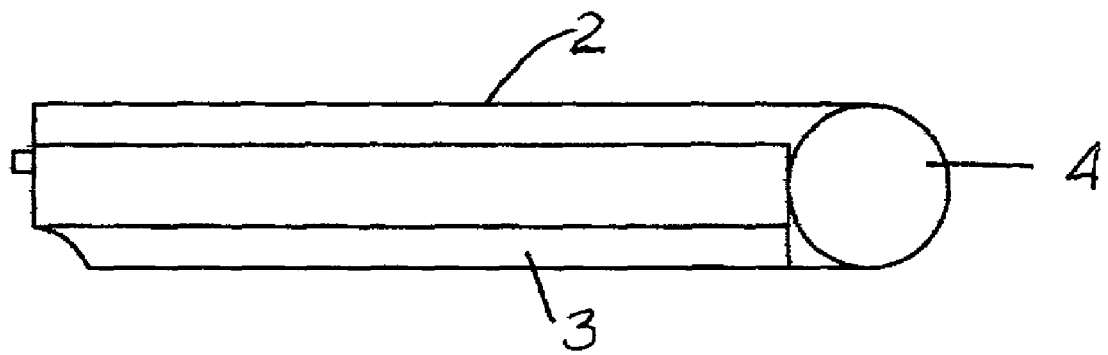
Figure 2:
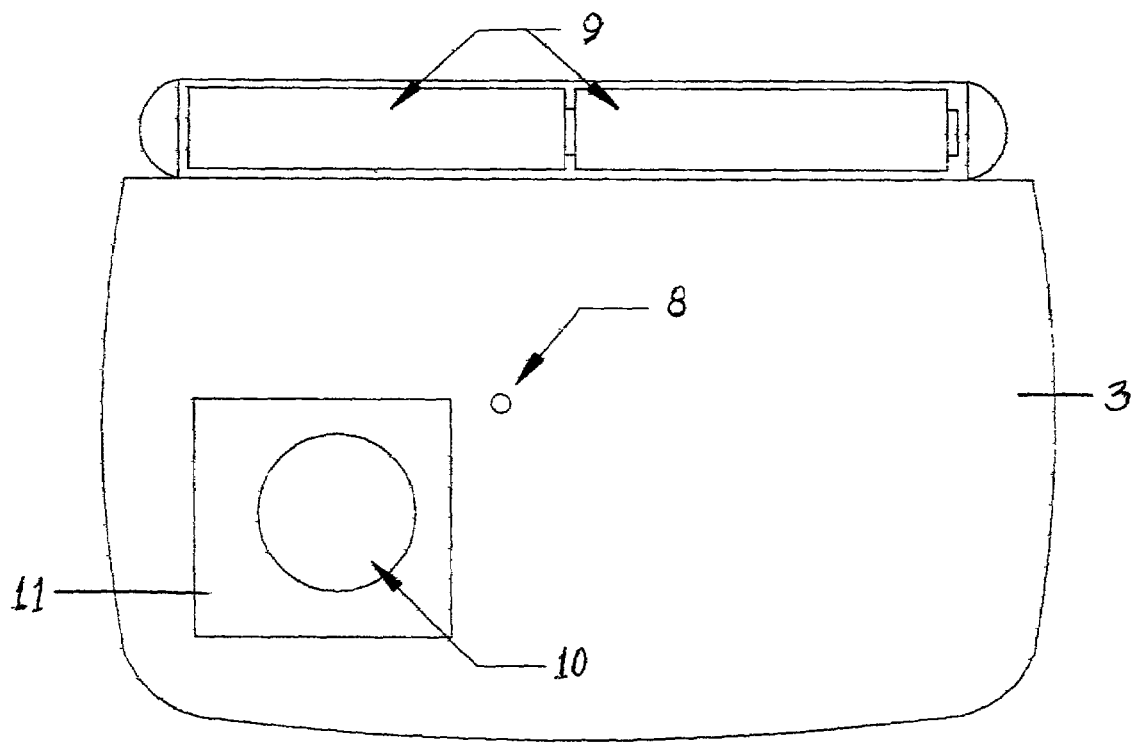

Reset key 8 is provided to allow the user to remove previously stored information and initialize all variables to default values. See reset key 8 adjacent battery compartment 9, back-up battery comparment 10 and cover 11 in FIG. 2C. Open and closed side views of housing 1 (consisting of upper and lower closure members, cover 2 and base 3) are shown in FIGS. 2A and 2B, respectively.

Figure 3:
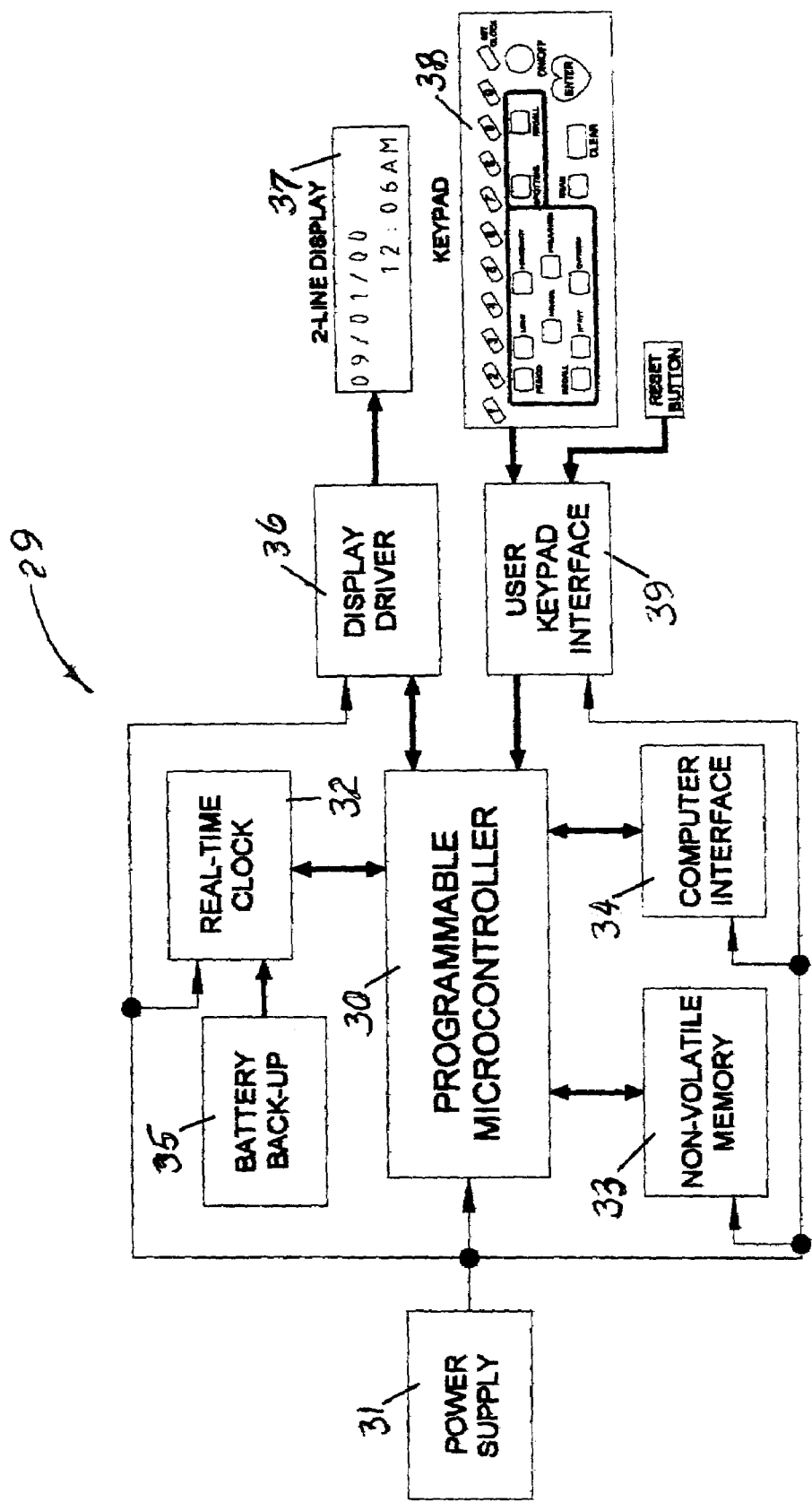
FIG. 3 is a block diagram of the operation of the present invention.
Figure 4:
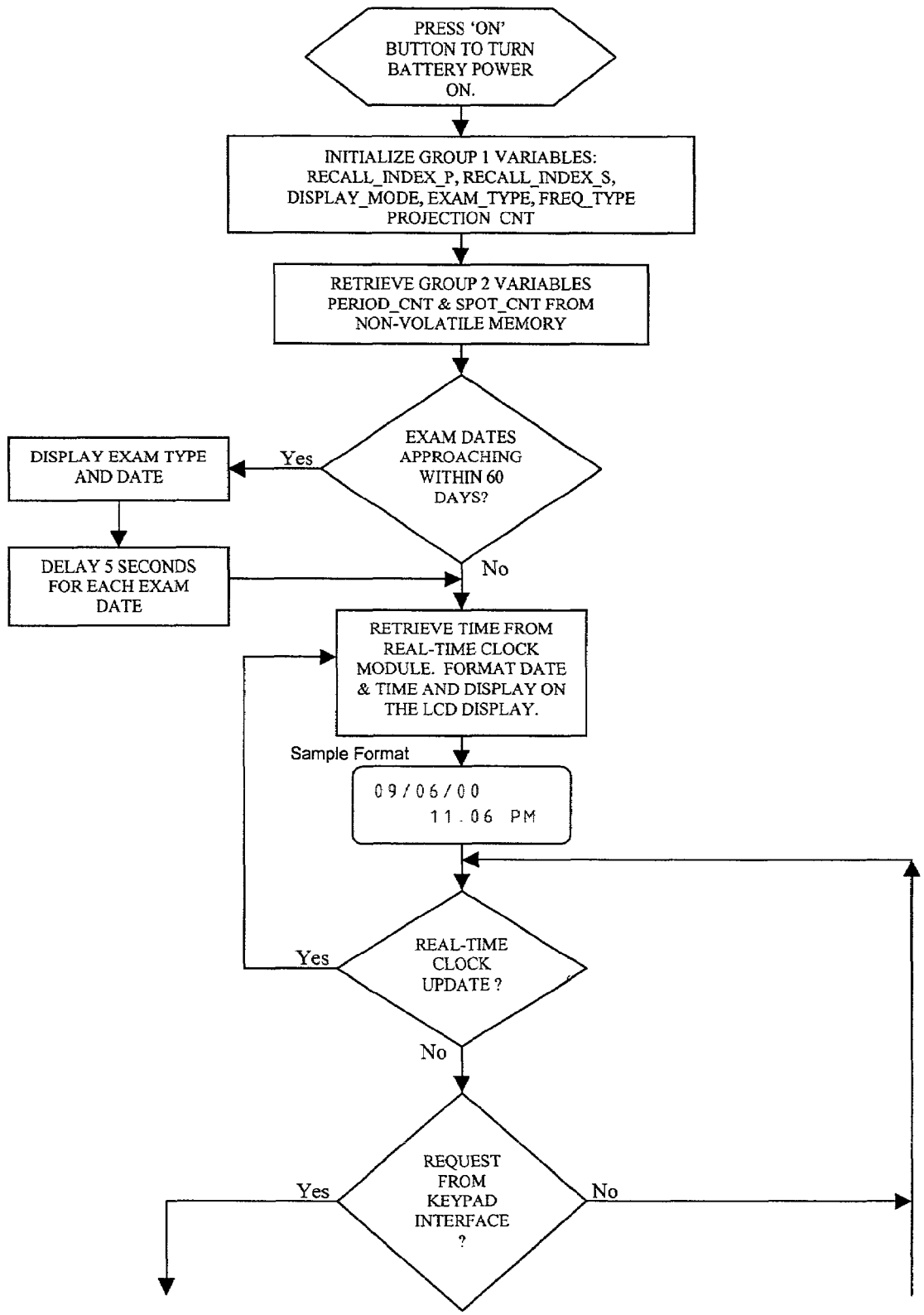
FIGS. 4A–H are flow charts of the program for the microcontroller of FIG. 3.
Figure 4:
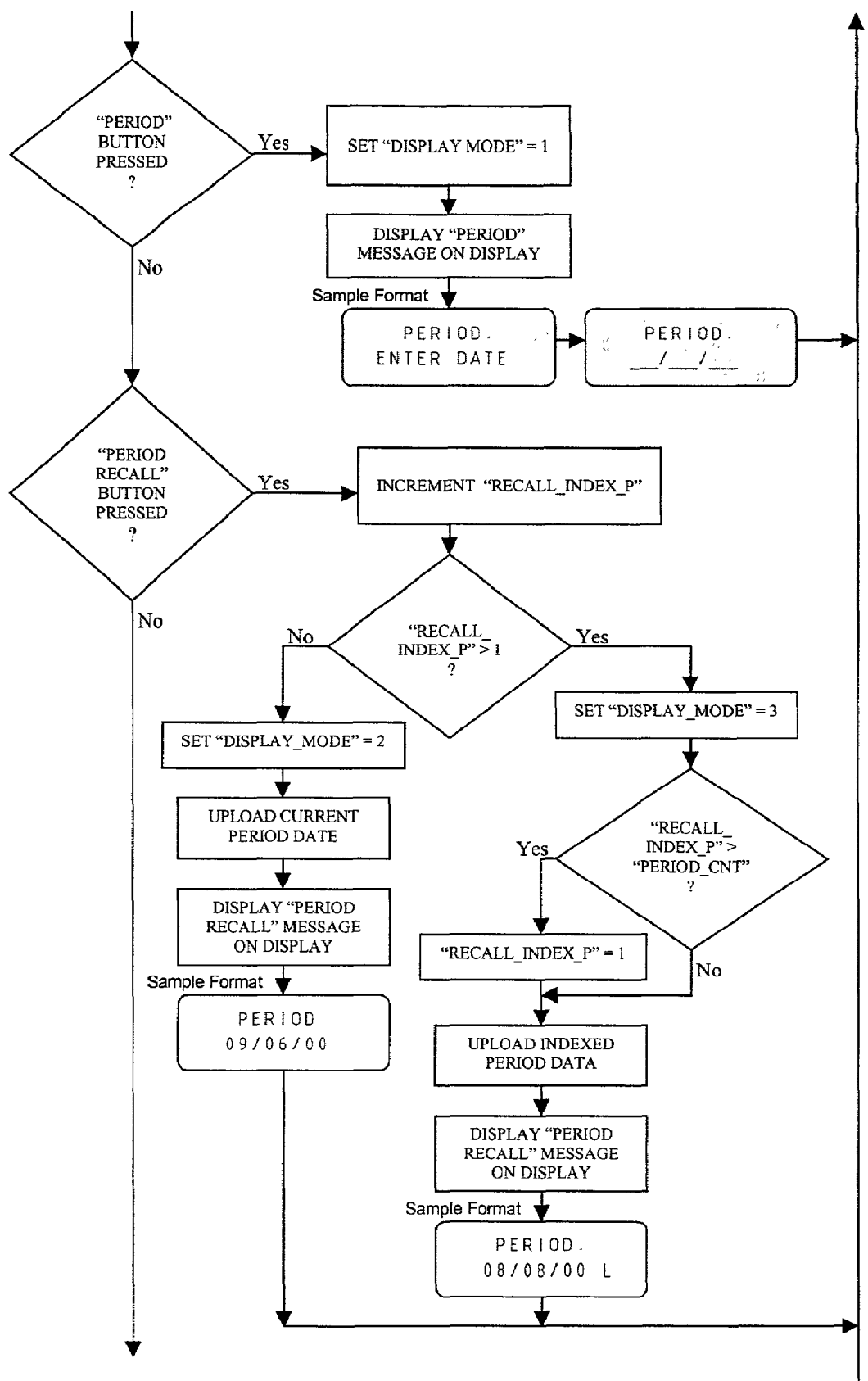
Figure 4:
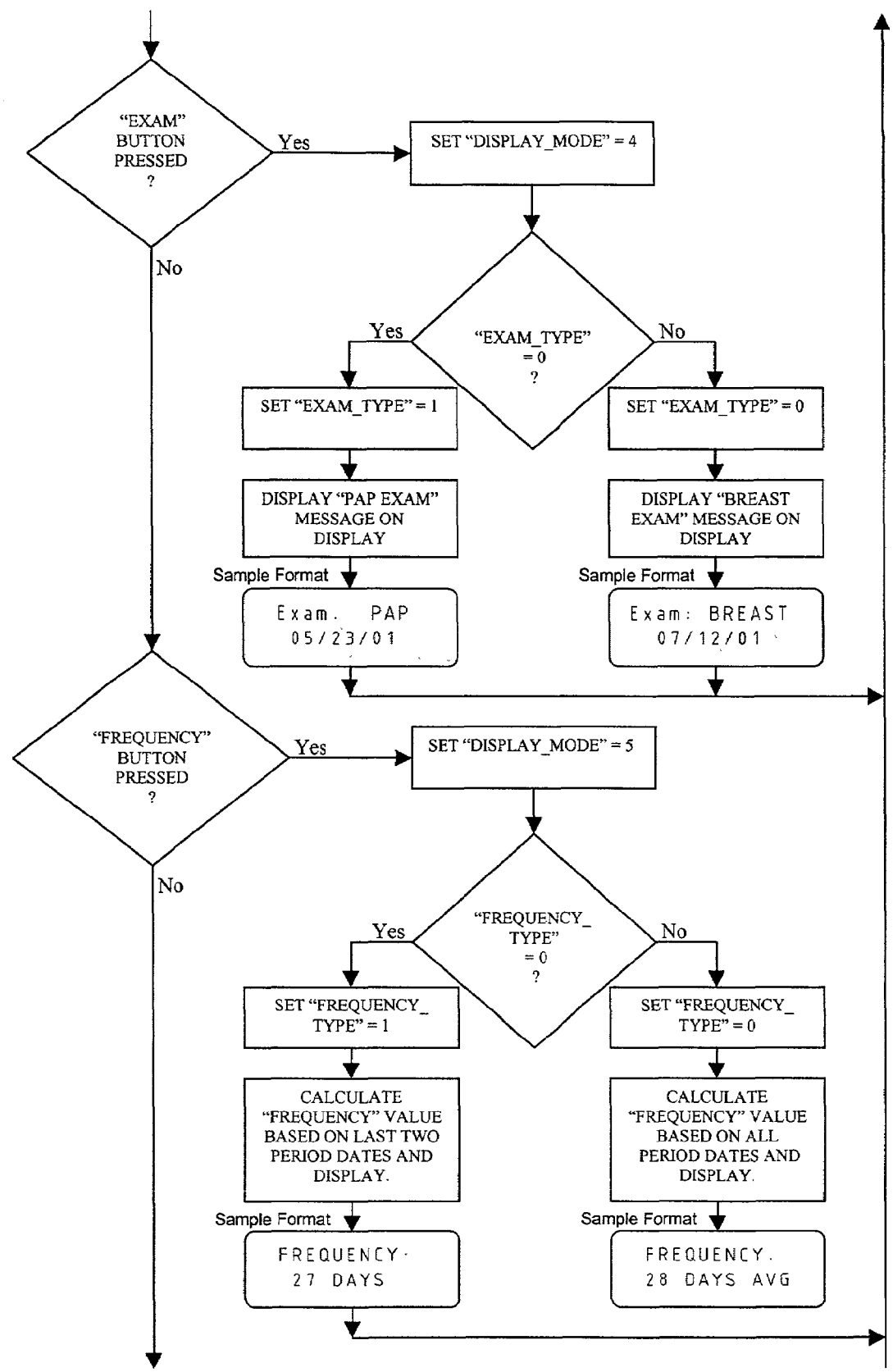
Figure 4:
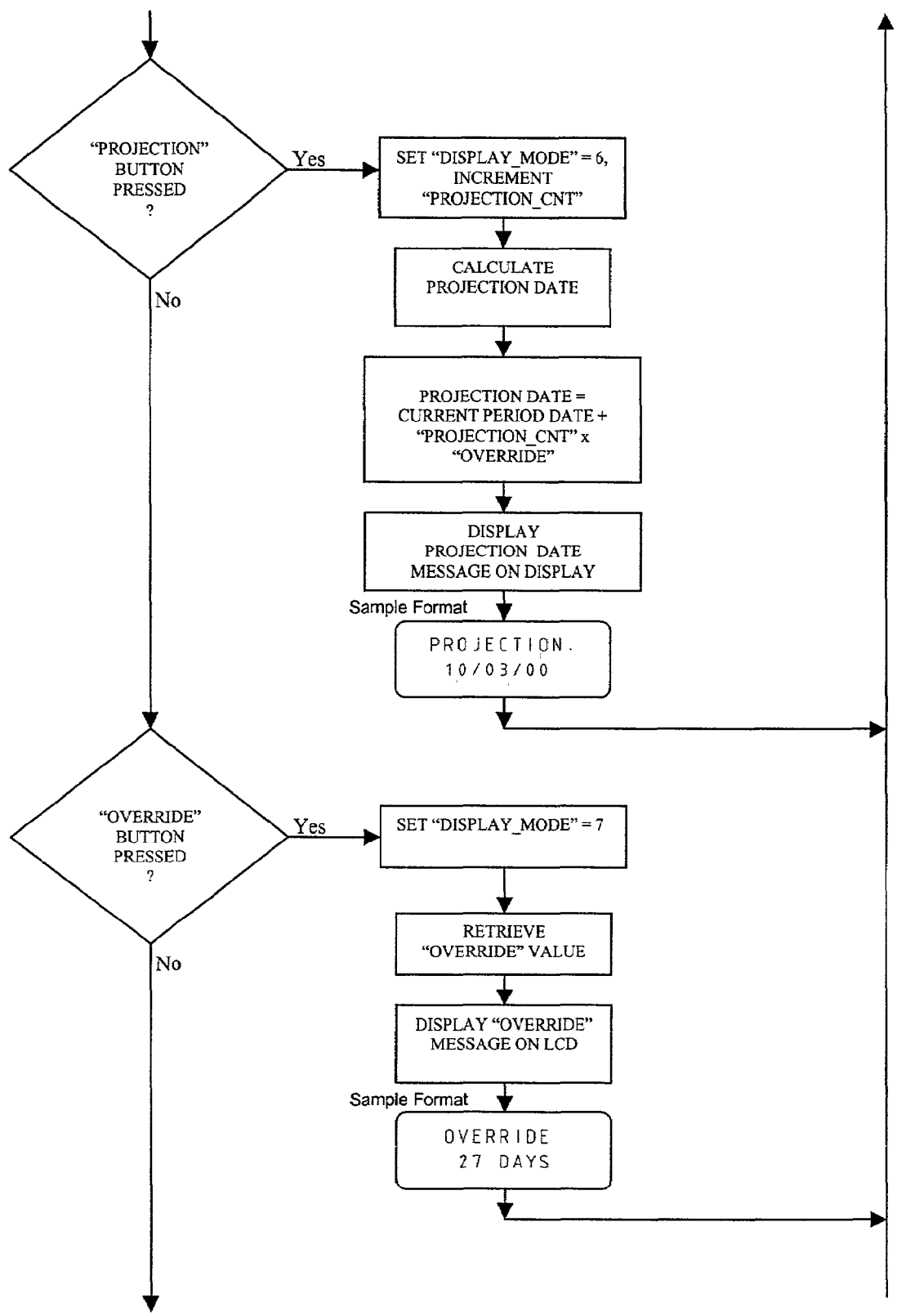
Figure 4:
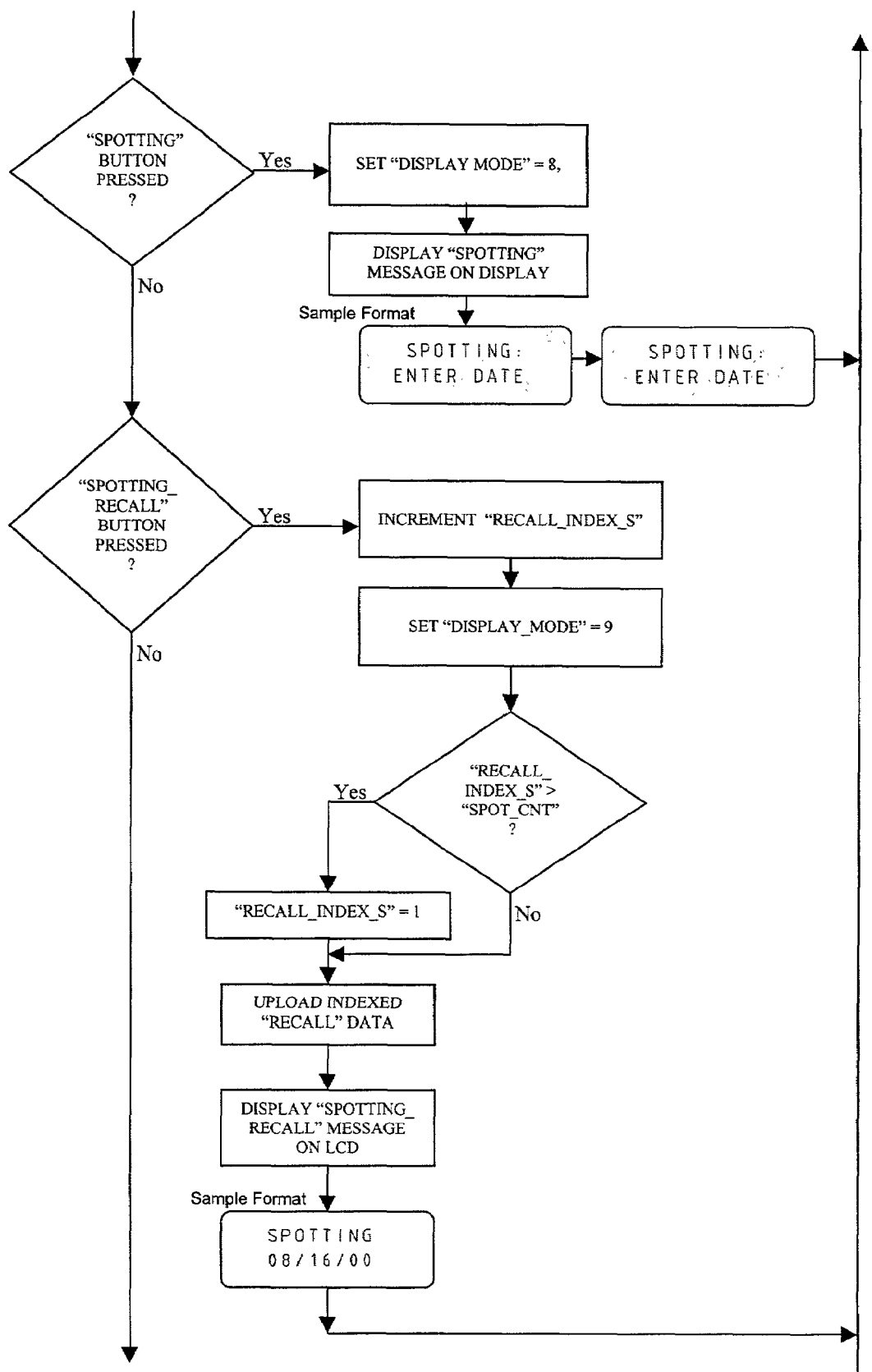
Figure 4:
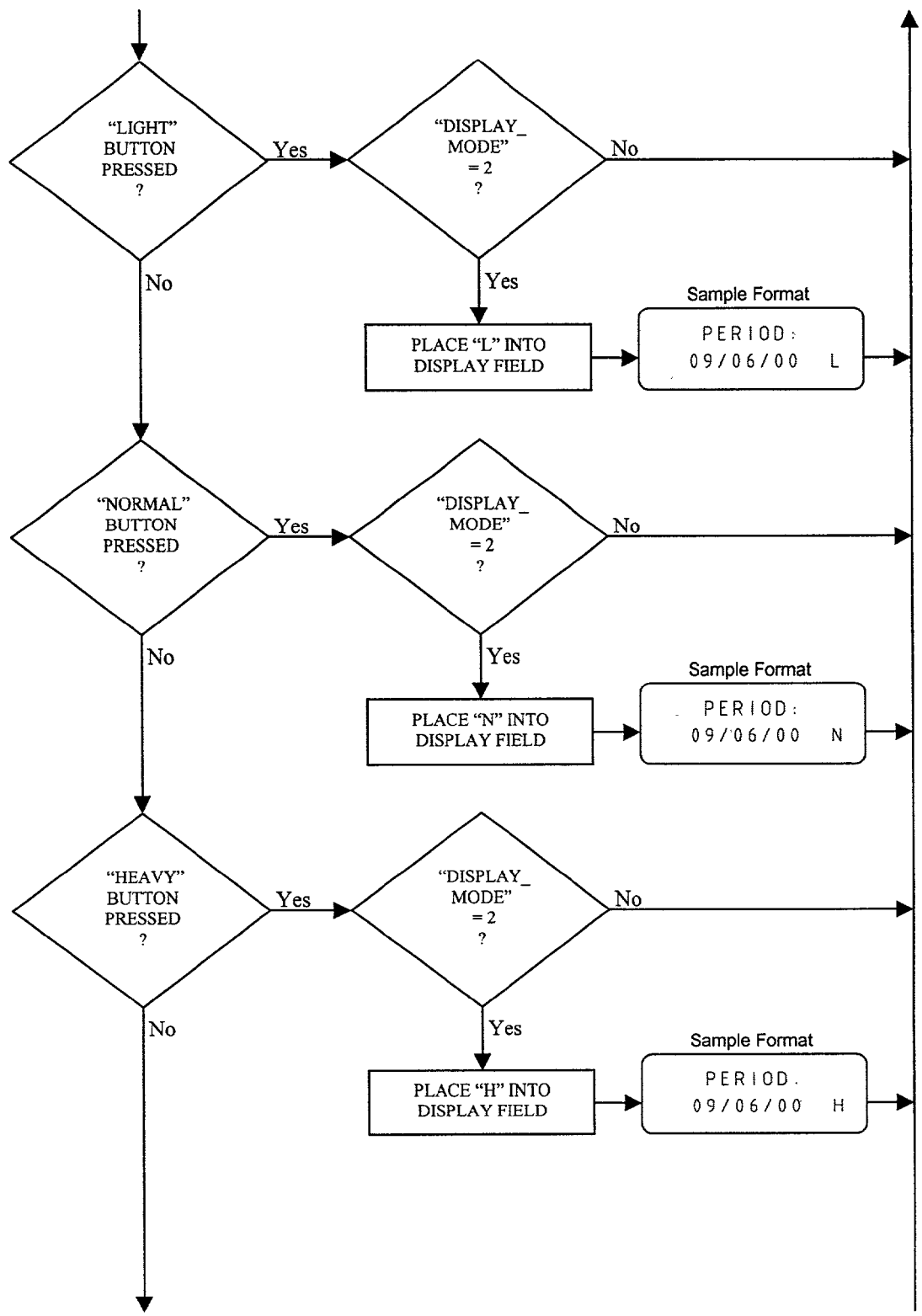
Figure 4:
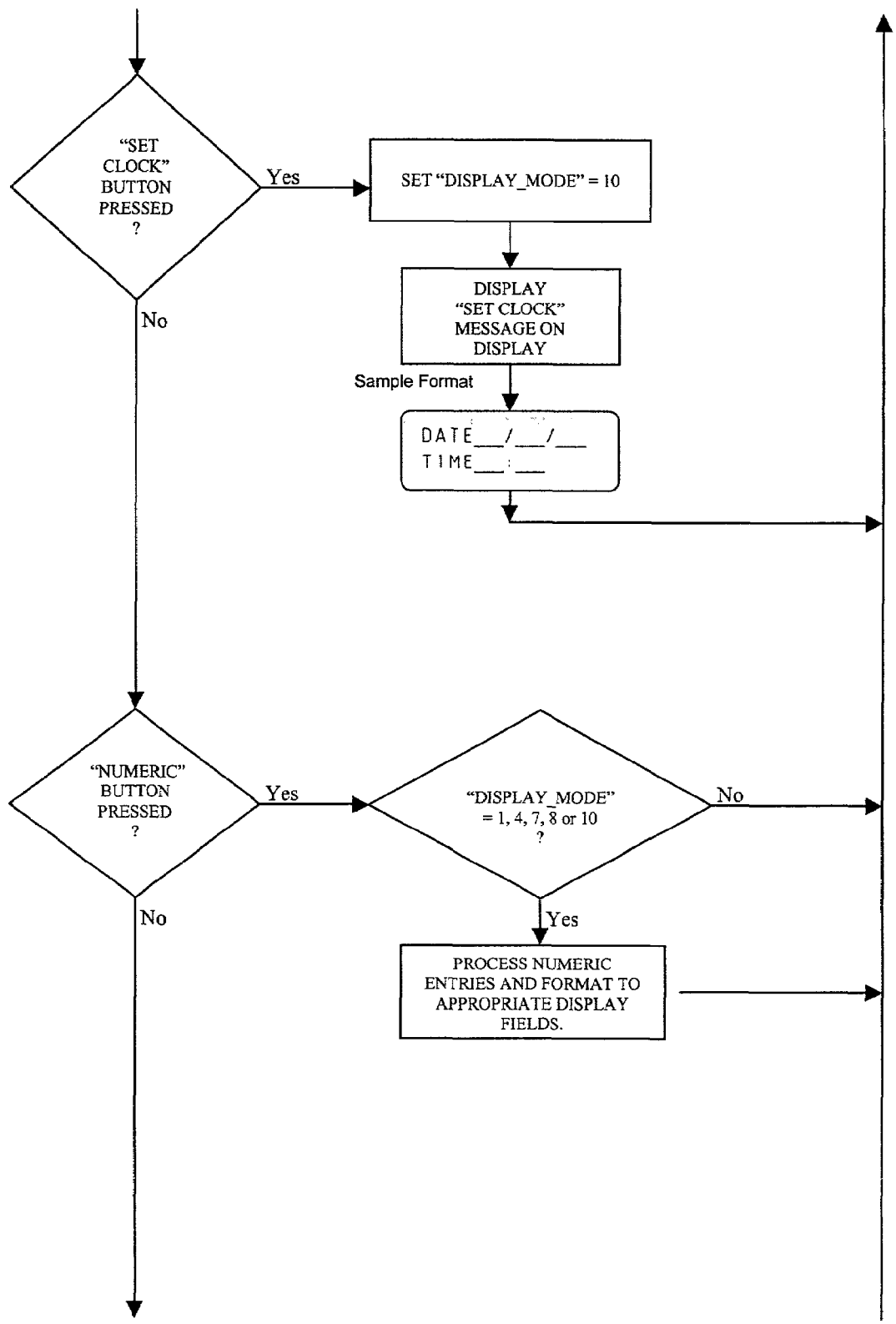
Figure 4:
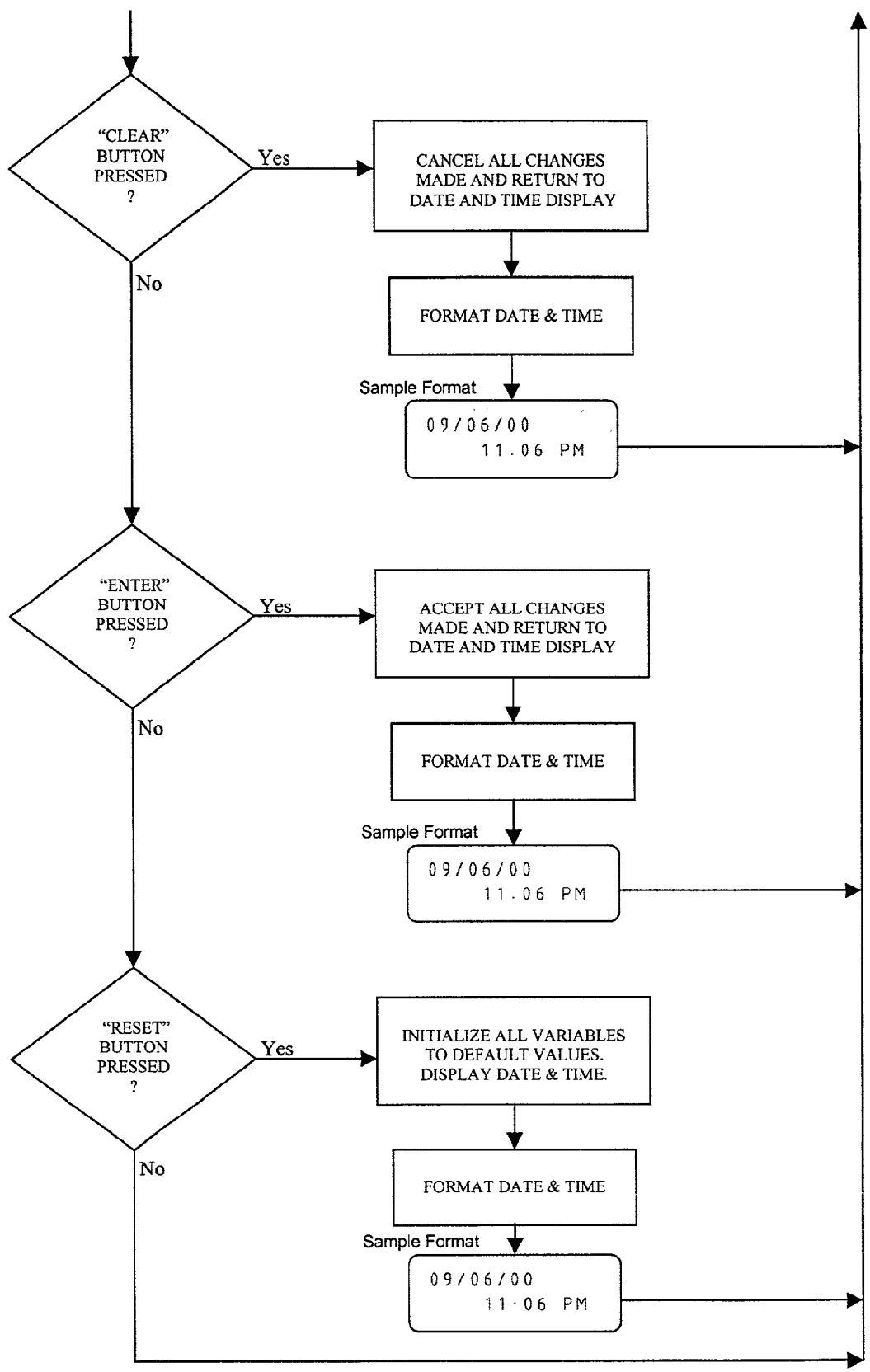

FIG. 3 shows operational system 29 for the device. The device is turned on by switch 12; power supply 31 signals programmable micro-controller 30 for operation. As shown in FIG. 3, Power Supply 31 powers all the components shown; however, real-time clock 32 is further provided with back-up battery 35 to maintain the operation of clock 32 when the system is turned off or loses power.

During the initial power activation, a software initialization occurs that initializes internal variables and updates 2-line LCD display 37. During the initialization, real-time clock 32 (with battery back-up 35) displays the current date (mm/dd/yy) on 2-line display 37 via driver 36. The display can be changed in response to an input from key pad 38 via user interface 39.

Internal variables are separated into two groups as follows: Group 1 and Group 2.

When system 29 of the device is turned on by switch 12, group 1 variables, namely, the recall of stored period and stored spotting dates, mode of displayed information, exam dates (PAP or breast type), frequency type (either the number of days between the last two period dates or the average number of days between all stored period dates) and the count of a month or months projected from the current month, up to twelve, are initialized to a fixed pre-determined value.

The variables are changed by the user through the operation of numeric keys on keypad 38 via user interface 39. However, Group 2 variables such as the period count, (stored period dates up to 12), the spotting count, (currently stored spotting dates up to 365) and the override are initialed to previous values that are retrieved from non-volitile memory 33 and are changed according to signals inputted by the user via keypad 38.

FIGS. 4A–4H show the operation of the device via a software flowchart.

Software Flowchart

On/off key 12 turns battery power on and off to the device.

When the device is powered on, a software initializaiton routine occurs that initializes internal variables and updates the information that is displayed on the Liquid Crystal Display (LCD). When the device is powered OFF, internal operation is stopped and the LCD becomes blank. The internal vaiables are separated into two groups: Group 1 variables are initialized to a fixed pre-determined value each time power is turned ON and changed according to subsequent button entries. Group 2 variables are initialized to a previous value that is retrieved from non-volatile memory within the device and changed according to subsequent button entries.

Group 1 variables include the following:
Recall_Index_P-Index Pointer to Array of Stored Period Dates.
Recall_Index S-Index Pointer to Array of Stored Spotting Dates.
Dispay Mode-Indicates Mode of displayed information.
Exam_Type_Indicates either PAP or breast type.
Frequency-Type Indicates either last two dates or average of all dates.
Projection Cnt Count of month projected from current month, up to 12.
Group 2 variables include the following:
Period_Cnt_Count of currently Stored Period Dates, up to 12.
Spot_Cnt—Count of currently Stored Spotting Dates, up to 365.
Override-The number of days between periods.

The information displayed on the LCD is initialized to the current Date and Time after an initial check is made for approaching exam dates. If no exam dates are scheduled, then date and time information is retrieved from the real-time-clock module and displayed; then a reminder message is displayed for each scheduled PAP or breast exam date appointment for 5 seconds before displaying the current date and time again. When an exam is scheduled and entered into the system, a reminder message for the specific exam date entered will not reappear for 302 days. The system will routinely display date and time. The device continually polls the keypad interface hardware waiting for any keypad key to be pressed.

Period key 14 prompts the user to enter new Period Information. When the Period key is pressed, a message prompting the user to enter a date is displayed on the LCD. The Display Mode variable is set equal to 1 to indicate that the date will be entered in a mm-dd-yy format. The Numeric keys are used for date entry. If the date entry is followed by the Enter button, the information is stored by the device and the Period_Cnt variable is incremented by one to maintain a current count of Period dates within the array. If the date entry is followed by the Clear key, the information is ignored and not stored by the device.

Period Recall key 15 scrolls through the array of stored Period Dates. When the Period Recall key is pressed, stored Period Dates are retrieved and displayed. The first Period date displayed is the current Period date and allows for updating of the flow information (Light, Normal or Heavy), The Display Mode variable is set equal to 2. Subsequent presses of the Period Recall key will scroll through the array until the maximum count of Period_Cnt is reached. The Display_Mode variable is set equal to 3.

Exam key 16 scrolls through the two stored exam dates. When the Exam key is pressed, stored Exam Dates are retrieved and displayed. The Display_Mode variable is set equal to 4. The first Exam type to be displayed is PAP Exam Type=0. The second Exam type to be displayed is Breast with Exam-Type=1. The Exam types are displayed alternately with subsequent button presses.

New Exam dates can be entered to overwrite the displayed date as required. If the date entry is followed by the Enter key, the information is stored by the device. If the date entry is followed by the Clear key, the information is ignored and not stored by the device.

Frequency key 17 displays the number of days between the last two periods or the average number of days between all stored Period dates. When the Frequency key is pressed, the number of days between periods is calculated. The Display_Mode variable is set equal to 5. The first Frequency type to be displayed is the calculated number of days between the current Period date and the last Period date with Frequency_Type=0. The second Frequency type to be displayed is the calculated average number of days between all stored Period dates with Frequency-Type=1. The Frequency types are displayed alternately with subsequent button presses.

Projection key 18 displays future Period dates relative to the current Period date.

When the Projection key is pressed, a future Period date is calculated relative to the current period date. The Display_Mode variable is set to equal 6. The projected future date is calculated relative to the current period date and the value stored by(as) the Override variable multiplied by the Projection_Cnt variable. Subsequent key presses display up to 12 future Period dates.

Override key 19 displays the number of days between periods. This value is used when calculating projection dates and is customizable to the individual user. When the Override key is pressed, the current value is retrieved and displayed. The Display-Mode variable is set equal to 7. A new Override value can be entered to overwrite the displayed value allowing customization for the individual user. If the value entry is followed by the Enter key, the information is stored by the device. If the value entry is followed by the Clear key, the information is ignored and not stored by the device.

Spotting key 20 prompts the user to enter new Spotting information. When the Spotting key is pressed, a message prompting the user to enter a date is displayed on the LCD. The Display_Mode variable is set equal to 8 to indicate that the date will entered as mm-dd-yy format. The Numeric keys are used for date entry. If the date entry is followed by the Enter key, the information is stored by the device and the Spot_Cnt variable is incremented by one to maintain a current count of Spotting dates within the array. If the date entry is followed by the Clear key, the information is ignored and not stored by the device.

Spotting Recall key 21 scrools through an array of stored Spotting Dates. When Spotting Recall key is pressed, stored Spotting Dates are retrieved and displayed. The Display_Mode variable is set equal to 9. Subsequent presses of the Spotting Recall key will scroll through the array until the maximum count of Spot_Cnt 365 is reached.

Light key 22 adds a flow parameter indicator to the current Period date display. When the Light key is pressed and Display_Mode=2, and "L" indicator is added to the Period display message. If the indicator entry is followed by the Enter key, the information is stored by the device. If the indicator entry is followed by the Clear key, the information is ignored and not stored by the device.

Normal key 23 adds a flow parameter indicator to the current Period date display.

When the Normal key is pressed and the Display-Mode-2, a "N" indicatior is added to the Period display message. If the indicator entry is followed by the Enter key, the information is stored by the device. If the indicator entry is followed by the Clear key, the information is ignored and not stored by the device.

Heavy key 24 adds a flow parameter indicator to the current Period date display. When the Heavy button is pressed and the Display-Mode=2, an "H" indicator is added to the Period display message. If indicator entry is followed by the Enter key, the information is stored by the device. If the indicator entry is followed by the Clear key, the information is ignored and not stored by the device.

Set clock key 25 allows the user to set or adjust the date and time of the real-time clock. When the Set Clock key is pressed, a message prompting the user to enter the date and time is displayed on the LCD. The Display_Mode variable is set equal to 10. Numeric keys are used for date and time entry. If the date and time entry is followed by the Enter key, the information is stored by the device. If the date and time entry is followed by the Clear key, the information is ignored and not stored by the device.

Numeric keys 26 allow the user to enter numeric data for those display modes that require them. When any of the Numeric keys are pressed, the Display_Mode variable is checked to determine if numeric data is required.

Numeric data is required for the following five display modes:
  Display_Mode=1: Period Date Entry;
  Display_Mode=4: Exam Date Entry;
  Display_Mode=7: Override Value Entry;
  Display_Mode=8: Spotting Date Entry;
  Display_Mode=10: Set Clock Date and Time Entry.

If the numeric entry is followed by the Enter key, the information is stored by the device. If the numeric entry is followed by the Clear key, the information is ignored and not stored by the device.

Clear key 27 allows the user to canel information being entered in the event of an error. When the Clear key is pressed, newly entered information is canceled and the display returns to current date and time display.

Enter key 28 allows the user to store information that is being entered via the keypad.

When the Enter key is pressed, newly entered information is stored and the display returns to current date and time display.

The device is provided with a recessed reset button 8. See FIG. 2C.

The Reset button allows the user to remove all previously stored information. When the Reset button is pressed, all variables are initialized to default values. The structure set forth is not considered limited by the disclosure supra. The structure as well as the electronic capabilities of the presently disclosed invention may be modified. Such modification included within the device is a RS232 port which enables the user on demand to have said aforementioned information printed on paper. The transferring and transporting of the device's information interfaced with user's personal computer via the RS232 port allows one such modification to occur. Other modifications could be made by one skilled in the art without departing from the spirit, scope and intent of the invention to meet demands and special applications.

This invention is limited only by the following claims.

We claim:

1. A portable electronic calculation device for generating gynecological tracking information, said device comprising:
   a housing having upper and lower portions;
   power means in said housing for energizing said device;
   an LCD display means in said housing arranged for viewing data;
   a programmable microcontroller, non-volatile memory and electrical component means located in said housing, said microcontroller programmed for receiving and calculating gynecological data to generate a display in response to an input of said gynecological data from at least one function or numeric key;
   a hinge member connecting said upper and lower housing portions whereby said lower portion is constructed and arranged to support said microcontroller and non-volatile memory;
   a keypad and keypad interface supported by the housing, said keypad including numeric and function keys for electrical communication with said microcontroller and non-volatile memory through said keypad interface;
   a spotting function key means on said keypad operable to record spotting dates by subsequent actuation of numeric keys to change a spotting variable by an increment of one to maintain a count of spotting dates within an array of spotting dates for storage in non-volatile memory.

2. The portable electronic device of claim 1 further comprising a
   spotting recall function key operable to scroll through spotting dates stored in said non-volatile memory up to a maximum count of three hundred and sixty-five.

3. A portable electronic calculation device for generating gynecological tracking information, said device comprising:
   a housing having upper and lower portions;
   power means in said housing for energizing said device:
   an LCD display means in said housing arranged for viewing data:
   a programmable microcontroller, non-volatile memory and electrical component means located in said housing, said microcontroller programmed for receiving and calculating gynecological data to generate a display in response to an input of said gynecological data from at least one function or numeric key;

a hinge member connecting said upper and lower housing portions whereby said lower portion is constructed and arranged to support said microcontroller and non-volatile memory;

a keypad and keypad interface supported by the housing, said keypad including numeric and function keys for electrical communication with said microcontroller and non-volatile memory through said keypad interface;

exam function key means on said keypad operable to enter PAP or Breast exam dates which dates are programmed for recall and display within sixty days of each exam date entered.

4. The portable electronic device of claim 3 further comprising a period
function key operable to store a period count variable incremented by one to maintain a count of period dates, each said period variable is stored in said non-volatile memory for future recall.

5. The portable electronic device of claim 3 further comprising a period
recall function key operable to recall period variables from said non-volatile memory, said recalled period variables are augmented to reflect a period fluid flow rate for each recalled period.

6. The electronic device of claim 5 further comprising a plurality of function keys
operable to assign a flow rate to each said recalled period variable.

7. The electronic device of claim 6 wherein each said assigned flow rate is light, normal or heavy.

8. The portable electronic tracking device of claim 3 further comprising a
frequency key operable to calculate a first and a second frequency type with actuation of said key.

9. The portable electronic tracking device of claim 3 further comprising a projection key operable to calculate a future period date or projection variable relative to a current period date or variable and the value is stored in said non-volatile memory as an override variable multiplied by the projection variable.

10. A portable electronic calculation device for generating gynecological tracking information, said device comprising:
a housing having upper and lower portions;
power means in said housing for energizing said device;
an LCD display means in said housing arranged for viewing data;
a programmable microcontroller, non-volatile memory and electrical component means located in said housing, said microcontroller programmed for receiving and calculating gynecological data to generate a display in response to an input of said gynecological data from at least one function or numeric key;
a hinge member connecting said upper and lower housing portions whereby said lower portion is constructed and arranged to support said microcontroller and non-volatile memory;
a keypad and keypad interface supported by the housing, said keypad including numeric and function keys for electrical communication with said microcontroller and non-volatile memory through said keypad interface;
an override function key operable to retrieve an override variable from said non-volatile memory and display said variable equal to the number of days between periods whereby said value is used to calculate a projection date or variable to customize the device to an individual user by selecting a new override value between fifteen and thirty-five that is specific to the user's cycle.

11. The electronic device of claim 10 wherein said power means includes a main and a back-up power source.

12. The electronic device of claim 11 wherein said hinge member is constructed to form a battery compartment for supporting said main power source.

13. The electronic device of claim 12 wherein said backup power source is housed in said lower housing portion.

14. The electronic device in device of claim 13 further comprising a mirror mounted in said upper portion of said housing.

15. The electronic device of claim 14 further comprising a clip and locking means
mounted on said upper and lower housing portions, respectively, for mechanically securing said housing in a closed position.

16. The electronic device of claim 10 wherein said display means is a two-line display.

17. The electronic device of claim 16 wherein the device is provided with a set clock
key which prompts a user, by flashing, when first activated to enter a date on one line of said two-line display and when actuated a second time a user is prompted, by flashing, to enter a time on the other line of said two-line display.

* * * * *